United States Patent [19]

Senturia

[11] Patent Number: 4,908,509
[45] Date of Patent: Mar. 13, 1990

[54] TRACTION AND REACTION FORCE MICROSENSOR

[75] Inventor: Stephen D. Senturia, Boston, Mass.

[73] Assignee: Massachusetts Institute of Technology, Cambridge, Mass.

[21] Appl. No.: 263,545

[22] Filed: Oct. 27, 1988

[51] Int. Cl.$^4$ .................................................. G01B 1/00
[52] U.S. Cl. ...................................... 356/373; 73/768; 250/227.11
[58] Field of Search .................... 250/227, 229; 73/81, 73/588, 768, 774, 150 A

[56] References Cited

U.S. PATENT DOCUMENTS

| | | | |
|---|---|---|---|
| 4,041,806 | 8/1977 | Klar | 73/150 A |
| 4,366,713 | 1/1983 | Gilmore et al. | 73/588 |
| 4,626,244 | 12/1986 | Reinicke | 604/151 |
| 4,679,567 | 7/1987 | Hanlon et al. | 73/708 |
| 4,730,496 | 3/1988 | Knecht et al. | 73/724 |
| 4,730,497 | 3/1988 | Rabensteiner et al. | 73/768 |
| 4,744,252 | 5/1988 | Stout | 73/768 |
| 4,809,552 | 3/1989 | Johnson | 73/517 R |
| 4,815,472 | 3/1989 | Wise et al. | 73/724 |
| 4,831,869 | 5/1989 | Fowler | 73/150 A |

OTHER PUBLICATIONS

The MIT Report, "New Inventions" section on Page, 11, Oct. 19, 1987.

*Primary Examiner*—David C. Nelms
*Assistant Examiner*—Stephane B. Allen
*Attorney, Agent, or Firm*—Hamilton, Brook, Smith & Reynolds

[57] ABSTRACT

A force sensor detects adhesion between a subject and a substrate through an adhesive. The sensor is embedded in the adhesive and is formed by two members which are displaceable relative to each other. A readout scheme detects displacement of the two members due to a force and reaction forces acting upon the sensor through the adhesive. Fiber optics may be employed in the readout scheme to provide an indication of displacement of the two members and thereby adhesion of the subject to the substrate.

52 Claims, 2 Drawing Sheets

TRACTION AND REACTION FORCE MICROSENSOR

BACKGROUND OF THE INVENTION

Many of today's products are manufactured in an assembly line fashion. Some parts of the product are manufactured in-house and other parts are manufactured by contracting companies or manufacturers. Often times a part manufactured by one company does not form the desired close fit to a part manufactured by a different company. The inexact fit of the two parts makes it difficult to bond the two parts together and increases the task of quality control of the overall product.

An example is the molding or trim of an automobile. Generally such trim is manufactured by a different company than the company who is manufacturing the body of the car to which the trim is to be attached. The area of the car body to which the trim is to be attached may have various curves in its contour. As a result, the trim must also have the same curves or be able to conform to the same curves in order to properly adhere to the body. Typically, an adhesive is applied at numerous sites along the body and the trim is placed over the adhesive and pressed into place. The adhesive may not hold the trim in place at all of the sites, particularly if there is some misfit between the parts. Accordingly, there is a need for a testing method and/or device which tests the quality of the bond made between an automobile molding or trim and a car body.

SUMMARY OF THE INVENTION

The present invention provides a sensor and method for detecting existence of forces within the adhesive, such as traction and reaction forces, due to the trim and car body adhering to each other, without destroying the bond created by the adhesive. The sensor is capable of fitting into a 3 mm or less thick layer of adhesive and is fabricated by techniques known in micromachining technology.

In particular, the sensor is suspended in and adhered to the adhesive applied to the car body. One surface of the sensor faces the trim through the adhesive and an opposite surface faces the car body through the adhesive. The sensor employs two members which are displaceable relative to each other with the application of a force across the adhesive. The displacement of the two members is sensed to provide an indication of adhesion between the trim and car body. The displacement is sensed by fiber optics, capacitance measurements between the two members or other means.

In one embodiment, the sensor employs a moveable shutter micromachined between two chambers. Light is supplied to one chamber and collected from the second chamber. When the shutter is open, light travels from the one chamber to the second chamber. When the shutter is closed, no light or less light travels from the one chamber to the second chamber. The shutter may be initially open or closed and changes to the opposite position (i.e. closed or open) by reaction forces, between the trim and car body due to adherence of the two to each other, brought about in response to a test force applied to the trim along an axis substantially normal to the trim. The change in shutter position causes a change in the amount of light collected from the second chamber. This change in amount of light collected provides an indication of the desired adhesion between the trim and the car body.

In accordance with one aspect of the present invention, light is preferably supplied to the one chamber and collected from the second chamber through fiber optics.

In a preferred embodiment, the sensor includes a first and second plate. The first plate has an outer surface which faces the trim through the adhesive and an inner surface opposite the outer surface. The second plate has an inner surface which faces the inner surface of the first plate. The inner surfaces of both plates are attached to each other along a periphery of the surfaces. The second plate has an outer surface opposite the inner surface and which faces the car body through the adhesive.

A first and second cavity sharing a common wall are formed between the two inner surfaces. The wall cooperates with one of the inner surfaces to provide a shutter between the first and second cavities. In an open position of the inner surface relative to the wall, the two cavities are able to communicate with each other across the wall. In a closed position of the inner surface relative to the wall, communication between the two cavities across the wall is disabled or decreased.

Light is provided in one of the cavities and is detected in the other cavity. This is preferably accomplished through two light guides in the inner surface of the first plate with one light guide leading from outside the adhesive to the one cavity and the second light guide leading from the outside to the other cavity. The light is communicated across the wall from the one cavity to the other cavity when the inner surface and wall are in the open position. The light is prevented from being communicated across the wall from the one cavity to the other cavity when the inner surface and wall are in the closed position. The inner surface and wall are changed between their relative positions of closed to open, or open to closed, by reaction forces between the trim and car body carried through the adhesive. The change in amount of light detected in the other cavity due to the changing of relative position of the wall and inner surface provided an indication of adhesion between the trim and the car body.

The reaction forces within the adhesive may be brought about by a test force applied to the trim along an axis substantially perpendicular to the trim (i.e. a pulling or pressing on the trim).

The two light guides and two cavities are preferably formed in the first and second plates respectively by chemical etching. Fiber optics are then readily employed in each of the light guides to provide light in one of the cavities and to collect or detect light in the other cavity.

The wall, or more accurately the top surface of the wall, may be initially in contact with but not attached to a central portion of the inner surface of the first plate. In this case, no or little light is initially communicated across the top surface of the wall from one cavity to the other. When the adhesive has created a bond between the trim and car body and the trim is slightly tugged away from the car body, the central portion of the inner surface of the first plate becomes displaced relative to the wall, and light is communicated across the top surface of the wall from the one cavity to the other cavity. The increase in the amount of light in the other cavity is detected and provides an indication of a proper adhesive bond between the trim and car body.

On the other hand, the wall and the central portion of the inner surface may initially be separated from each other such that light is communicated across the wall from one cavity to the other cavity. If the adhesive has created a proper bond between the trim and car body, the pushing or pressing of the trim toward the car will result in the closing of the inner surface relative to the wall. In turn, less or no light will be communicated across the wall from the one cavity to the other. The decrease in the amount of light in the other cavity will be detected and will provide an indication of a proper bond by the adhesive.

The dimension from the outer surface of the first plate to the back surface of the second plate is about ½ mm or less. In addition, the finished lateral dimensions of the sensor are about 1 mm on each side such that the sensor does not interfere with the bond between the trim and car body created by the adhesive.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
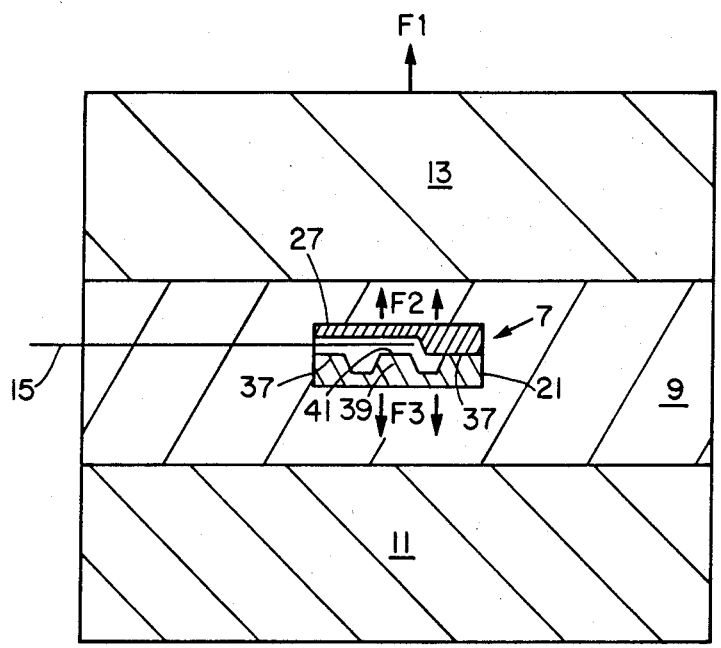
FIG. 1 is a cross-section along the line I—I of the force sensor shown in FIG. 2 embodying the present invention as applied to the testing of adherence of an adhesive between a car molding and car body.

A schematic illustration of one application of a force sensor embodying the present invention is provided in FIG. 1. A force sensor 7 is embedded in a layer of foam adhesive 9 which is applied in either a continuous stream or in a series of beads to a portion of a car body 11 during assembly. Each bead of the foam layer of adhesive 9 is about ⅛ inch thick and is long and wide enough to totally surround the sensor 7. A piece of molding or trim 13 is positioned over and pressed onto the adhesive 9 to affix the trim to the car body 11. A readout assembly 15 leads from the sensor to outside the trim-adhesive area for use by the tester. A slight pulling of the molding 13 away from the car body 11 creates a test force F1 which tests the traction forces F2, F3 between the adhesive 9 and molding 13 and between the adhesive 9 and car body 11 respectively. The sensor 7 detects the existence of traction forces F2 and F3 and provides through readout assembly 15 an indication of the quality of the bond created by the adhesive 9.

In a similar manner, the test force F1 may be applied in a direction toward the molding 13 by the tester pressing on the molding 13 toward car body 11. This test force tests reaction forces between the adhesive 9 and molding 13 and between the adhesive 9 and car body 11 respectively which are like traction forces F2 and F3 but opposite in direction. In this case, a sensor of a modified design of the present invention detects the existence of the reaction forces and provides through readout assembly 15 an indication of the quality of the bond created by the adhesive 9.

Figure 2:
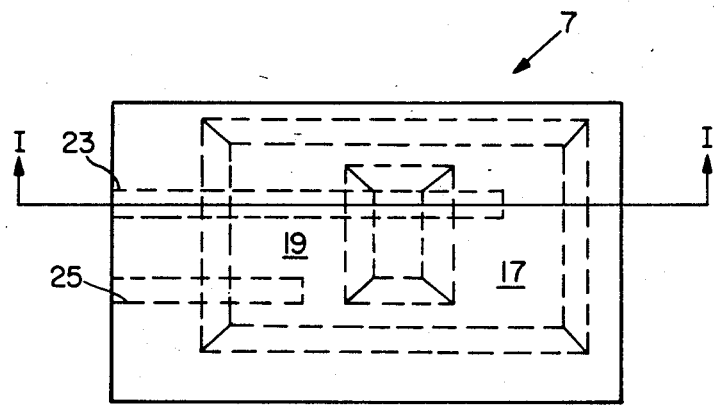
FIG. 2 is a plan view of the force sensor of FIG. 1.
Figure 3A:
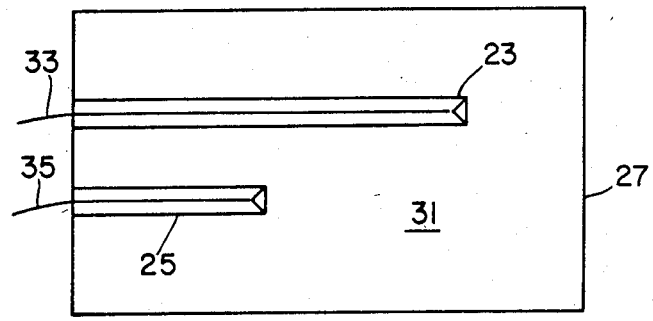
FIG. 3a is a bottom view of an upper plate of the force sensor of FIG. 1.
Figure 3B:
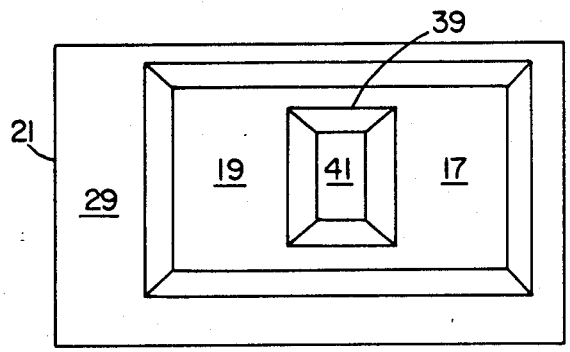
FIG. 3b is a plan view of a lower plate of the force sensor of FIG. 1.

More detailed views of the force sensor 7 are shown in FIGS. 2-3b. FIG. 2 is an overview of force sensor 7. The sensor is formed by two chambers 17 and 19 provided in a lower plate 21 as shown in FIGS. 3b, and two grooves 23, 25 provided in an upper plate 27 as shown in FIG. 3a. The two chambers each have an open side at the surface 29 of lower plate 21. Similarly the two grooves 23, 25 each have an open side at the surface 31 of upper plate 27. Surface 31 of the upper plate 27 is positioned adjacent to the surface 29 of the lower plate 21 such that the two grooves 23, 25 face the two chambers 17, 19. The first groove 23 is of a length such that it leads from outside the sensor to a central region of one of the chambers, say 17 for purposes of illustration. The second groove 25 is of a length such that it leads from outside the sensor to a central region of the second chamber 19. The grooves house optic fibers 33 and 35 to provide the readout assembly of the sensor 7. Optic fiber 33 in the first groove 23 carries light from an outside source into the one chamber 17. The optic fiber 35 in the second groove 25 collects light from inside the second chamber 19 and carries the collected light to the tester for a reading of the amount of light detected in the second chamber.

The upper and lower plates 27, 21 are bonded together along the periphery of adjacent surfaces 31 and 29 by suitable means such as glues, adhesives and the like. The bonded areas are generally indicated by reference number 37 in FIG. 1. The wall 39 which separates the two chambers 17, 19 from each other has a top surface which is level with the surface 29 of the lower plate 21. Top surface 41 of the wall 39 is in close proximity with or in contact with (but not bonded to) a central area of the surface 31 of the upper plate 27. The contact made between wall top surface 41 and upper plate surface 31 prevents the traveling of light from the one chamber 17, over the wall 39 and into the second chamber 19. On the other hand, if the top surface 41 of the wall and the upper plate surface 31 are slightly separated from each other, light is allowed to travel from the one chamber 17, over the top surface of the wall 39 and into the second chamber 19. In this case, a greater amount of light is detected in the second chamber 19 and the tester is made aware of the separation between the top surface 41 of the wall and the surface 31 of the upper plate 27.

Such a separation between the top surface of the wall 39 and central area of upper plate surface 31 occurs if a successful bond exists between the adhesive and car body and between the adhesive and molding, and if a test force F1 is applied along an axis substantially normal to the molding such that the net traction on the lower plate 21 causes a downward (i.e. toward the car body) deformation of the floor areas in each chamber of the lower plate which in turn moves the wall 39 away from the upper plate 27. Said another way, if the adhesive bond to the car is successful, traction forces F2 and F3 of FIG. 1 between the adhesive and the molding and between the adhesive in car body respectively are relatively large and cause the upper and lower plates 27, 21 to be separated at non-bonded areas when test force F1 is applied. If traction force F3 is relatively small because the adhesive bond to the car is weak or unsuccessful, then the wall 41 does not move relative to upper plate 27, the wall top surface 41 and upper plate surface 31 are not separated, and no increase in light in the second chamber 19 is detected in response to the test force F1.

The wall 39 of force sensor 7 of FIG. 1 serves as a shutter between the one and second chamber and may be said to be initially closed. A force sensor with an initially open shutter embodying the present invention is provided in FIG. 4. The basic construction and application of sensor 43 is similar to that of force sensor 7 in FIG. 1. The sensor 43 of FIG. 4 has a lower plate 45 housing two chambers 47, 49 and an upper plate 51 with two grooves or light guides 53, 55 (only one groove 53 shown). The two plates 51, 45 are positioned such that the two grooves associate with the two chambers 47, 49, and the two plates 51, 45 are bonded together about the periphery of their adjacent surfaces. The wall 55 separating the two chambers 47, 49 is of a height which is shorter than the periphery surface of the lower plate 45 with respect to the base 57 of the plate. Hence, the top surface 69 of wall 55 is separated from a center area of the surface 67 of the upper plate 51 by a distance of about 1 micron to about 10 microns. The separation distance is large enough to allow light generated in the first chamber 47 (49) through one of the grooves 53 to travel from the first chamber, over the wall 55 and into the second chamber 49 (47). The amount of the light within the second chamber 49 (47) is collected and detected by fiber optics 65 housed by the second groove similar to that described in the sensor 7 of FIG. 1.

The wall 55, acting as a shutter between the two chambers 47, 49, changes from its initially open position to a closed position when a test force F4 is applied to the molding 13 by the tester pressing on the molding toward the car body 11. If the adhesive bond to the car is successful, reaction forces F5, F6 between the adhesive 9 and molding 13 and between the adhesive 9 and car body 11 respectively, are generated. Reaction forces F5 and F6 act on upper and lower plates 51, 45 respectively, in directions toward each other such that the top surface 69 of wall 55 is pushed toward and makes contact with a central region of upper plate surface 67. Once contact is made between wall top surface 69 and upper plate surface 67, the shutter is closed and light is prevented from being communicated over the wall 55 from the first chamber 47, (49) to the second chamber 49 (47). Consequently, a decrease in the amount of light is detected in the second chamber 49 (47) and provides an indication of a successful bond of the molding 13 to the car 11.

Conversely, if the reaction force F5 between the adhesive 9 and the molding 13 is small due to a weak or no bond between the molding and the adhesive, then the pressing test force F4 does not cause the shutter to close and no decrease in the amount of light is detected. Hence, an unsuccessful adhesive bond is indicated.

Figure 4:
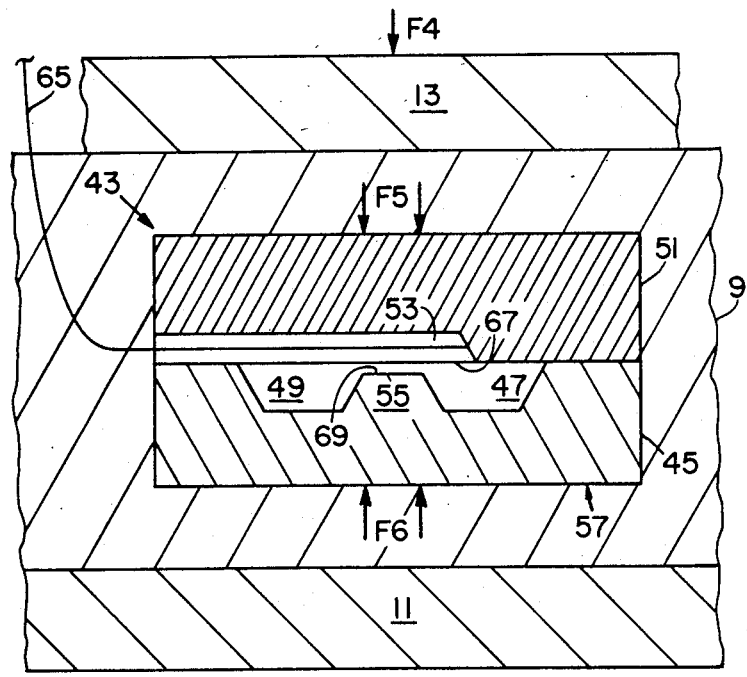
FIG. 4 is a cross section of another sensor embodying the present invention which has an initially open shutter.

The force sensor 43 of FIG. 4 is embedded within the adhesive 9 applied to the car body 11 during assembly in a manner similar to that of force sensor 7 of FIG. 1. The tester in this case, however, presses the molding 13 toward the car body 11 instead of pulling the molding away from the car body to test the adherence of the adhesive 9. In either case, the test force is applied along an axis which is substantially perpendicular or geometrically normal to the molding and car body, and the sensor experiences reaction forces brought about in response to the test force due to adhesion of the adhesive 9 to both the molding 13 and car body 11. In the first described sensor 7, the reaction (i.e. traction) forces cause the shutter to open and consequently cause an increase in the amount of light to be communicated from the one chamber to the second chamber which is detected to provide an indication of sensed adherence between the molding and car body. In the latter described sensor 43, the reaction forces cause the shutter to close and consequently cause a decrease in the amount of light communicated from the first chamber to the second chamber which is detected to provide indication of sensed adherence between the molding 13 and the car body 11.

The readout scheme of the foregoing sensors is not limited to light and optical means. Alternatively, a capacitance measurement may be made between the top surface of the wall and the central area of the upper plate surface to detect a change in the shutter position from open to close or vice versa, and thereby detect the quality of adherence. In general, detection of a change in a capacitance measurement between the upper and lower plates is suitable to provide an indication of displacement of the plates relative to each other and thereby an indication of an adhesive bond. Many known and common electronic techniques for sensing such change in capacitance may be employed.

In addition, the readout scheme is not required to provide a quantitative indication of adherence. Hence, there are no concerns about precision and calibration in the sensors of the present invention. The readout scheme is only required to provide an indication of relative displacement of two working members of the sensor and thereby an indication of the existence of an adhesive bond between the molding and car body by the applied adhesive.

The grooves and chambers of sensors 7 and 43 are preferably formed by chemically etching two silicon wafers. Two fiber carrying grooves are isotropically, or alternatively, anisotropically etched into one silicon wafer. The use of masking techniques known in the art allows great precision in the etching of the grooves such that the grooves are etched to a width just slightly larger than the diameter of the optic fiber to snugly hold the optic fiber. Likewise, known masking techniques are used to anisotropically etch the two chambers separated by a wall in a second silicon wafer. In the case of the sensor with the initially open shutter, a shallow region is etched across a silicon wafer. A middle portion of the shallow region is masked as well as the outer edges and back of the silicon wafer. The wafer is then etched anisotropically to form the two chambers separated by the wall with a top surface at a height shorter than the height of the peripheral surface with respect to the back of the wafer.

Using such micromachining techniques, the foce sensors of the present invention can inexpensively be mass fabricated. In addition, the sensor has finished lateral dimensions of about 1 mm on each side and an overall thickness from the outer surface of the lower plate to the outer surface of the upper plate of about ½ mm. With such small dimensions the sensor does not interfere with the bond between the molding and car body created by the adhesive.

It is understood that other fabrication techniques, materials and finished dimensions are suitable.

While the invention has been particularly shown and described with reference to a preferred embodiment thereof, it will be understood by those skilled in the art that various changes in form and details may be made therein without departing from the spirit and scope of the invention as defined by the appended claims.

I claim:

1. A sensor for detecting adhesion between a subject and a substrate being adhered together with an adhesive, the sensor comprising:
   a housing suspended within and adhered to the adhesive, the housing having first and second members displacable relative to each other with application of a force and a reaction force across the adhesive; and
   means for sensing the displacement of the first and second members.

2. A sensor as claimed in claim 1 wherein the means for sensing include fiber optics.

3. A sensor as claimed in claim 1 wherein the first and second members include first and second plates which form between each other two cavities separated by a wall, displacement of the first and second plates relative to each other with application of a force and reaction force across the adhesive changing communication between the two cavities across the wall; and
   the means for sensing displacement of the first and second plates detects change in communication between the two cavities across the wall.

4. A sensor as claimed in claim 3 wherein the first and second plates are formed by silicon micromachining.

5. A sensor as claimed in claim 3 wherein the means for sensing includes means for providing light in one of the two cavities and means for detecting light in the other cavity.

6. A sensor as claimed in claim 5 wherein the means for providing light and the means for detecting light include fiber optics.

7. A sensor for detecting adhesion between a subject and a substrate being adhered together with an adhesive, the sensor comprising:
   a housing having a first chamber and a second chamber in communication with each other, the housing being suspended within and adhered to the adhesive;
   a shutter positioned between the first and second chamber, a change in position of the shutter causing a change in communication between the first and second chambers, the shutter changing position by reaction forces brought about between the subject and substrate due to adhesion between the subject and the substrate; and
   means for detecting change in position of the shutter to provide an indication of adherence between the subject and substrate.

8. A sensor as claimed in claim 7 wherein the sensor has a thickness of no greater than about ½ mm.

9. A sensor as claimed in claim 7 wherein the first and second chambers are formed by chemical etching.

10. A sensor as claimed in claim 7 wherein the means for detecting change in position of the shutter includes:
    means for providing light within one of the first and second chambers; and
    means for detecting light within the other of the first and second chambers, an amount of light communicated from the one chamber to the other being changed with the changing of position of the shutter, the means for detecting light within the other chamber detecting a change in the amount of light being communicated from the one chamber to the other when the shutter changes position in response to reaction forces and providing an indication of sensed adhesion between the subject and substrate.

11. A sensor as claimed in claim 9 wherein chemical etching includes micromachining in silicon.

12. A sensor as claimed in claim 10 wherein the means for providing light includes fiber optics.

13. A sensor as claimed in claim 10 wherein the means for detecting light includes fiber optics.

14. A test sensor for detecting adhesion of a subject to a substrate by an adhesive, the sensor comprising:
    a first plate having an outer surface which faces the subject through the adhesive, and an inner surface opposite the outer surface;
    a second plate having:
        an inner surface which faces and associates with the inner surface of the first plate and
        an outer surface opposite the inner surface and which faces the substrate through the adhesive,
    a first and second cavity having a wall in common being formed between the inner surfaces, the wall being displaceable relative to one of the inner surfaces such that communication between the first and second cavities across the wall is changed, the wall being displaced by adhesion reaction forces between the subject and substrate through the adhesive brought about in response to a test force applied to the subject; and
    means for detecting displacement of the wall to provide an indication of adhesion of the subject to the substrate.

15. A test sensor as claimed in claim 14 wherein a dimension from the outer surface of the first plate to the outer surface of the second plate is no greater than about ½ mm.

16. A test sensor as claimed in claim 14 wherein the test force is applied to the subject along an axis substantially perpendicular to the outer surface of the first plate.

17. A test sensor as claimed in claim 14 wherein the first and second cavities are formed by chemical etching.

18. A test sensor as claimed in claim 14 wherein the means for detecting displacement includes:
    means for providing light within one of the first and second cavities; and
    means for detecting light within the other of the first and second cavities, a change in amount of light communicated from the one cavity to the other occurring when the wall is displaced relative to the one inner surface, the means for detecting light detecting the change in the amount of light communicated from the one cavity to the other and providing an indication of sensed adhesion of the subject to the substrate.

19. A test sensor as claimed in claim 17 wherein chemical etching includes etching in silicon.

20. A test sensor as claimed in claim 18 wherein the means for providing light includes fiber optics.

21. A test sensor as claimed in claim 18 wherein the means for detecting light includes fiber optics.

22. A test sensor as claimed in claim 18 wherein one of the inner surfaces has a first and second light guide, the first light guide for the means for providing light within the one of the first and second cavities, the second light guide for the means for detecting light within the other of the first and second cavities.

23. A test sensor as claimed in claim 22 wherein the means for providing light includes fiber optics.

24. A test sensor as claimed in claim 22 wherein the means for detecting light includes fiber optics.

25. A test sensor as claimed in claim 22 wherein the first and second light guides are formed by chemical etching.

26. A test sensor as claimed in claim 25 wherein chemical etching includes etching in silicon.

27. A traction force sensor comprising:
(a) a first plate having an outer surface and an inner surface opposite the outer surface;
(b) a second plate having:
  (i) an inward surface which faces the inner surface of the first plate, the inward and inner surfaces being attached to each other along a periphery of each surface;
  (ii) an outward surface opposite the inward surface; and
  (iii) a first and second chamber between the inward and outward surfaces, both chambers having an opening at the inward surface and sharing a common wall,
  the wall having a top surface at the inward surface which faces and makes contact with but is unattached to the inner surface of the first plate such that communication between the first and second chambers across the top surface of the wall is disabled;
  the inner surface of the first plate and the top surface of the wall breaking contact with each other and enabling communication between the first and second chambers across the top surface of the wall when forces causing traction between the first and second plates are applied to both the outer surface of the first plate and the outward surface of the second plate;
(c) means for providing light within the first chamber; and
(d) means for detecting light within the second chamber, the light detecting means detecting a change in amount of light within the second chamber when the inner surface of the first plate and the top surface of the wall break contact with each other, the light detecting means thereby providing an indication of traction forces existing about the sensor.

28. A sensor as claimed in claim 27 wherein the means for providing light include fiber optics.

29. A sensor as claimed in claim 27 wherein the means for detecting light include fiber optics.

30. A sensor as claimed in claim 27 wherein a thickness dimension from the outer surface of the first plate to the outward surface of the second plate is less than about ½ mm.

31. A sensor as claimed in claim 27 wherein the first and second chambers are formed by chemical etching.

32. A sensor as claimed in claim 27 wherein the inner surface of the first plate has a first and second light guide, the first light guide leading from outside the sensor to the first chamber, the second light guide leading from outside the sensor to the second chamber.

33. A sensor as claimed in claim 31 wherein chemical etching includes silicon micromachining.

34. A sensor as claimed in claim 32 wherein the means for providing light and the means for detecting light include fiber optics.

35. A sensor as claimed in claim 32 wherein the first and second light guides are formed by chemical etching.

36. A sensor as claimed in claim 35 wherein chemical etching includes silicon micromachining.

37. A sensor for detecting existence of pressing and reaction forces comprising:
a first plate having an outer surface and an inner surface opposite the outer surface;
a second plate having:
  (i) an inward surface which faces the inner surface of the first plate, the inward surface of the second plate and the inner surface of the first plate being attached to each other along a periphery of each surface;
  (ii) an outward surface opposite the inward surface; and
  (iii) a first and second chamber between the inward and outward surfaces, both chambers having an opening at the inward surface and sharing a common wall, the wall having a top surface at the inward surface which faces and is out of contact with a central portion of the inner surface of the first plate such that the first and second chambers are able to communicate to each other across the top surface of the wall;
the central portion of the inner surface of the first plate and the top surface of the wall making contact with each other and changing communication between the first and second chambers across the top surface of the wall when forces causing the first and second plates to be pressed toward each other exist at both the outer surface of the first plate and the outward surface of the second plate;
means for providing light within the first chamber, the light subsequently being communicated to the second chamber; and
means for detecting light within the second chamber, the light being communicated from the first chamber, the light detecting means detecting a change in amount of light within the second chamber when the inner surface of the first plate and the top surface of the wall make contact with each other, the light detecting means thereby providing an indication of pressing forces existing about the sensor.

38. A sensor as claimed in claim 37 wherein the means for providing light includes fiber optics.

39. A sensor as claimed in claim 37 wherein the means for detecting light includes fiber optics.

40. A sensor as claimed in claim 37 wherein a thickness dimension from the outer surface of the first plate to the outward surface of the second plate is less than about ½ mm.

41. A sensor as claimed in claim 37 wherein the first and second chambers are formed by chemical etching.

42. A sensor as claimed in claim 37 wherein the inner surface of the first plate has a first and second light guide, the first light guide leading to the first chamber from outside the sensor and housing the means for providing light within the first chamber, the second light guide leading from outside the sensor to the second chamber and housing the means for detecting light within the second chamber.

43. A sensor as claimed in claim 41 wherein chemical etching includes silicon micromachining.

44. A sensor as claimed in claim 42 wherein the means for providing light and the means for detecting light include fiber optics.

45. A sensor as claimed in claim 42 wherein the first and second light guides are formed by chemical etching.

46. A sensor as claimed in claim 45 wherein chemical etching includes silicon micromachining.

47. A method of sensing adhesion between a subject and a substrate being adhered together by an adhesive, the steps comprising
    (a) suspending within and adhering to the adhesive a sensor having first and second members displaceable relative to each other with application of a force and a reaction force across the adhesive; and
    (b) sensing displacement of the first and second members to provide an indication of sensed adhesion between the subject and substrate.

48. A method as claimed in claim 47 wherein the step of sensing displacement includes employing fiber optics.

49. A method of testing adhesion between a subject and a substrate being adhered together by an adhesive, the steps comprising:
    (a) suspending within the adhesive a sensor having:
        a housing having a first chamber and a second chamber in communication with each other;
        a shutter positioned between the first and second chamber for changing communication between the first and second chambers by changing position, the shutter changing position by reaction forces brought about between the subject and the adhesive and between the adhesive and substrate due to adherence between the subject and the substrate;
    (b) providing light in one of the first and second chambers, a change in amount of light communicated from the one chamber to the other chamber occurring when the shutter changes position; and
    (c) detecting a change in amount of light communicated from the one chamber to the other due to the shutter changing position by reaction forces, the detecting of the change in amount of light providing an indication of sensed adhesion between the subject and substrate.

50. A method as claimed in claim 49 wherein the step of providing light includes employing fiber optics.

51. A method as claimed in claim 49 wherein the step of detecting light includes employing fiber optics.

52. A method as claimed in claim 49 further comprising the step of applying a test force to the subject along an axis substantially perpendicular to the sensor to bring about the reaction forces.

* * * * *